United States Patent [19]
Wilk

[11] Patent Number: 5,152,279
[45] Date of Patent: Oct. 6, 1992

[54] RETRACTOR AND ASSOCIATED METHOD FOR USE IN LAPAROSCOPIC SURGERY

[76] Inventor: Peter J. Wilk, 185 W. End Ave., New York, N.Y. 10023

[21] Appl. No.: 792,379

[22] Filed: Nov. 15, 1991

[51] Int. Cl.$^5$ .............................................. A61B 1/32
[52] U.S. Cl. ........................................ 128/17; 128/20
[58] Field of Search .................. 128/17, 20; 606/198; 604/28, 26

[56] References Cited

U.S. PATENT DOCUMENTS

| | | | |
|---|---|---|---|
| 817,973 | 4/1906 | Hausmann | 128/17 |
| 3,517,128 | 6/1970 | Hines | |
| 3,744,481 | 7/1973 | McDonald | 128/17 |
| 3,810,462 | 5/1974 | Szpur | 128/20 |
| 4,350,151 | 9/1982 | Scott | 128/17 |
| 4,702,230 | 10/1987 | Pelta | 128/20 |
| 4,726,356 | 2/1988 | Santilli et al. | 128/20 |
| 4,966,130 | 10/1990 | Montaldi | 128/17 |
| 5,052,373 | 10/1991 | Michelson | 128/20 |

Primary Examiner—Gene Mancene
Assistant Examiner—Michael Lynch
Attorney, Agent, or Firm—R. Neil Sudol; Henry D. Coleman

[57] ABSTRACT

A retractor instrument for use in laparoscopic surgery, comprises an elongate frame or holder and a substantially rigid retractor member movably mounted to the frame. A first retainer component is mounted to frame for maintaining the retractor member in substantially parallel relation to the frame during an insertion of the retractor instrument through a patient's abdominal wall and partially into the patient's abdominal cavity in a laparoscopic procedure. A second retainer component is connected to the frame for maintaining the retractor member in an angled orientation with respect to the frame during utilization of the retractor instrument to displace an internal body organ of the patient in the laparoscopic procedure.

24 Claims, 5 Drawing Sheets

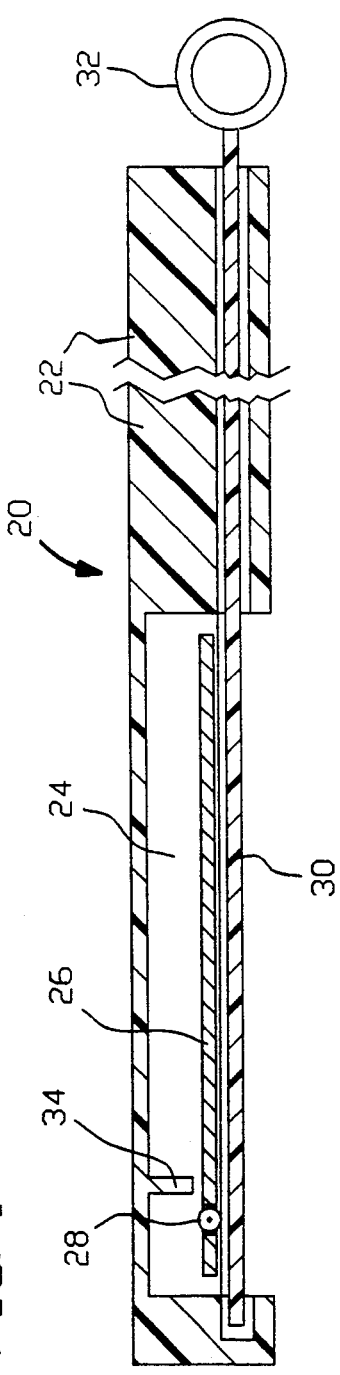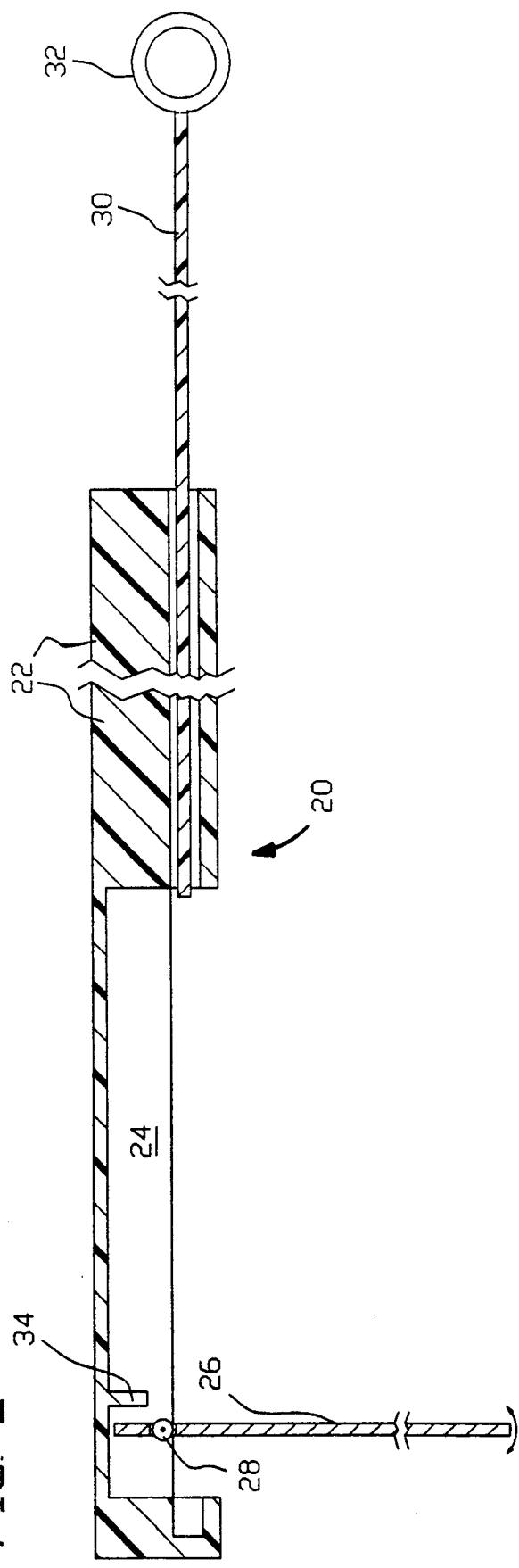

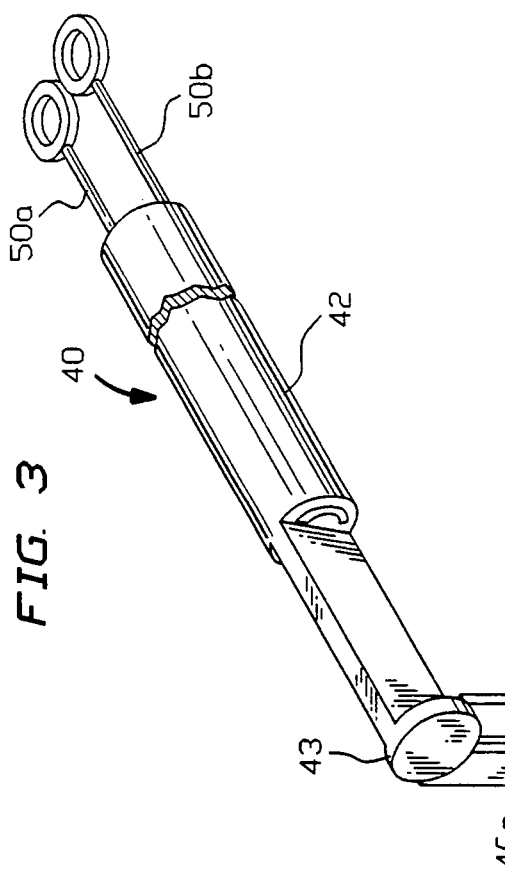
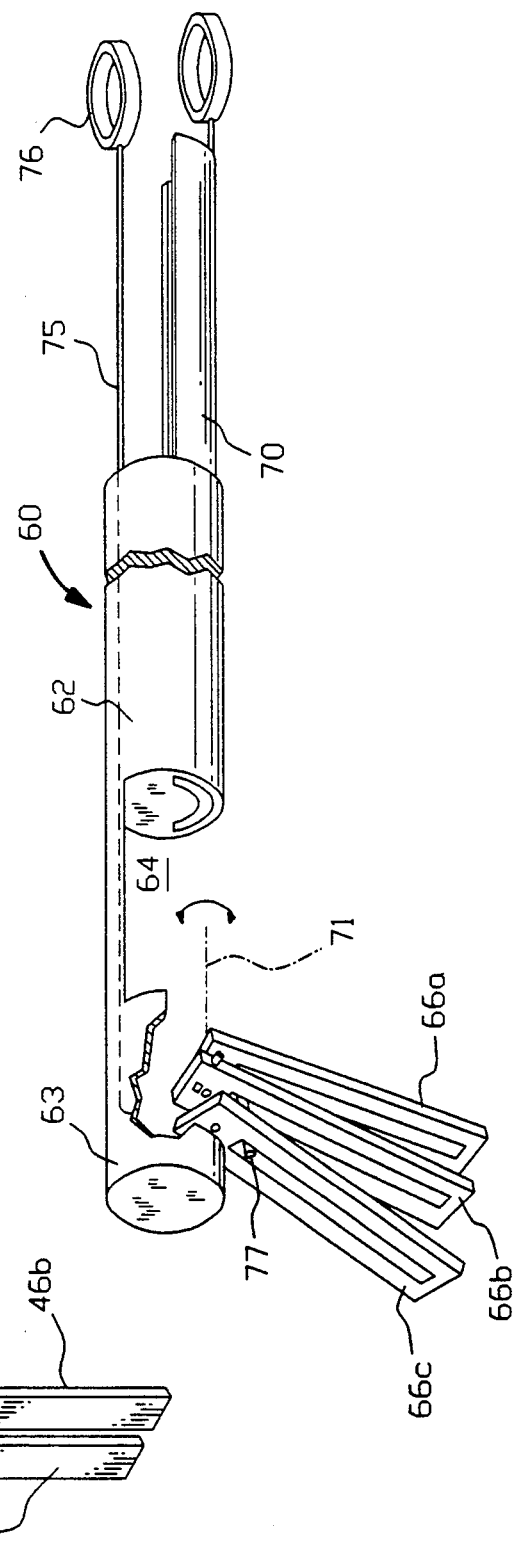

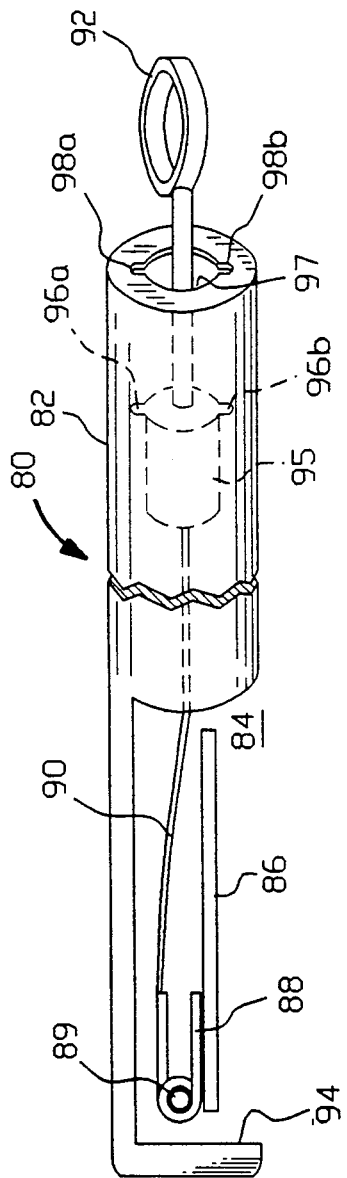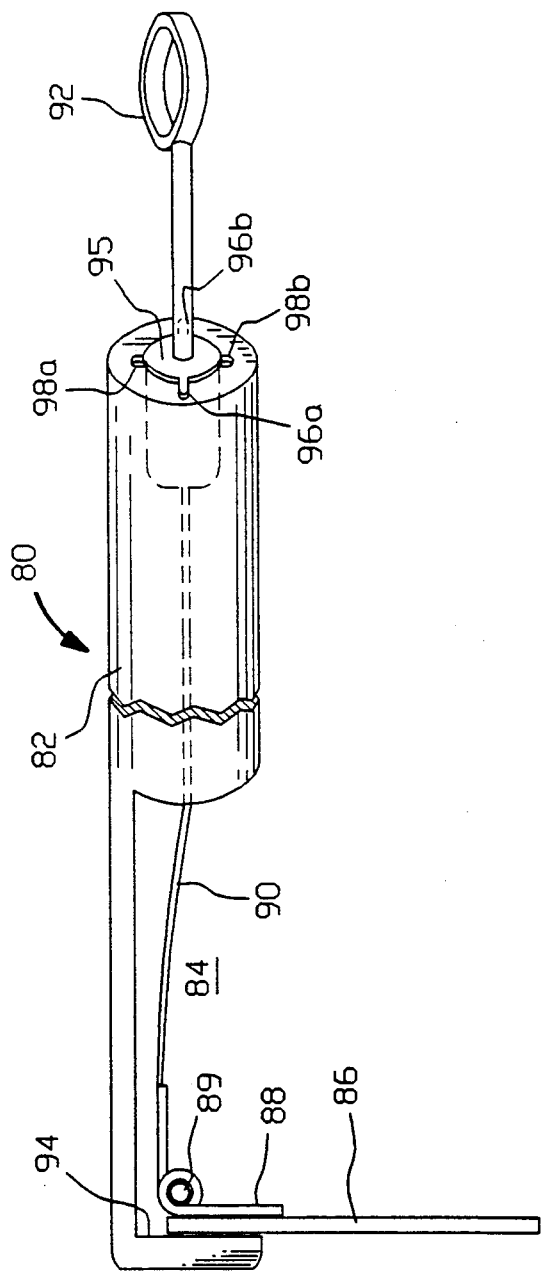

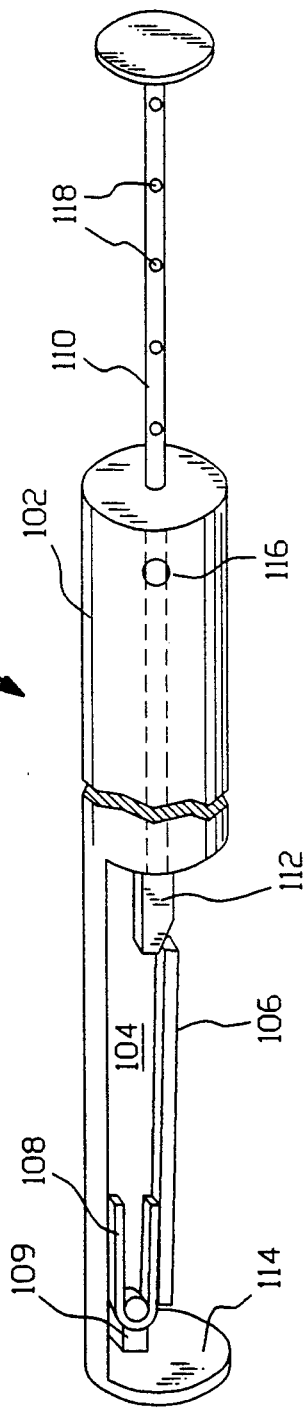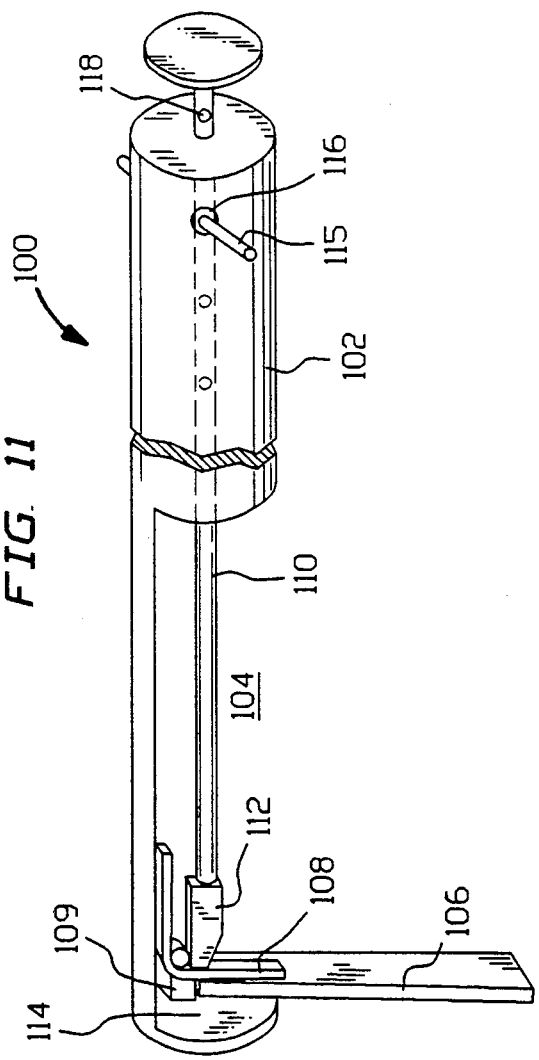

RETRACTOR AND ASSOCIATED METHOD FOR USE IN LAPAROSCOPIC SURGERY

BACKGROUND OF THE INVENTION

This invention relates to a surgical instrument. More particularly, this invention relates to a retractor for use in laparoscopic surgery. This invention also relates to an associated surgical method.

In laparoscopic surgery, one or more openings are made in a patient's abdominal wall, usually by piercing the wall with the aid of a trocar. A laparoscope is inserted through one of the openings to enable a surgeon to see organs and tissues which are located in the patient's abdominal cavity. Usually, operating instruments such as grasping forceps and cutting tools are inserted into the abdominal cavity through ancillary openings made in the abdominal wall.

Some internal organs or tissues are disposed under other organs when the patient is lying on his or her back (the normal posture during laparoscopic surgery). The overlying organs must be lifted or otherwise displaced prior to operating on the underlying organs. Generally, a grasping forceps is used to grip an overlying organ and pull it upwardly to provide access to the desired surgical site. This procedure is frequently cumbersome, if not ineffective, to adequately expose the underlying organs and tissues.

OBJECTS OF THE INVENTION

An object of the present invention is to provide an improved technique for temporarily displacing an internal body organ of a patient during laparoscopic surgery.

Another object of the present invention is to provide an associated surgical instrument for use in laparoscopic surgery.

Another, more particular, object of the present invention is to provide a laparoscopic surgical retractor.

A further particular object of the present invention is to provide such a retractor which is easy to use and inexpensive to fabricate.

SUMMARY OF THE INVENTION

A retractor instrument for use in laparoscopic surgery, comprises, in accordance with the present invention, an elongate frame or holder and a substantially rigid retractor member movably mounted to the frame. A first retainer component is mounted to frame for maintaining the retractor member in substantially parallel relation to the frame during an insertion of the retractor instrument through a patient's abdominal wall and partially into the patient's abdominal cavity in a laparoscopic procedure. A second retainer component is connected to the frame for maintaining the retractor member in an angled orientation with respect to the frame during utilization of the retractor instrument to displace an internal body organ of the patient in the laparoscopic procedure.

Pursuant to another feature of the present invention, the frame is provided at a distal end with a recess for receiving and at least partially enclosing the retractor member during the insertion of the retractor instrument through the patient's abdominal wall and partially into the patient's abdominal cavity.

Preferably, the first retainer component takes the form of or includes a locking element for holding the retractor member in the recess in the frame. More preferably, the locking element is a slider member slidably mounted to the frame.

Pursuant to another feature of the present invention, the retractor member is pivotably mounted to the frame. This feature of the invention enables a surgeon to change the orientation of the rigid retractor member with respect to the frame by simply rotating the frame about a longitudinal axis. The retractor member then pivots with respect to the frame in response to the force of gravity.

According to a more particular feature of the present invention, the retractor member is pivotably mounted to the frame via a universal joint. This feature of the invention is especially advantageous in the event that there are two or more essentially retractor members pivotably mounted to the frame. The retractor members can then pivot about two axes from a storage configuration in which the retractor members are in spaced parallel planes to a use configuration in which the retractor members are located in substantially the same plane.

Pursuant to an additional feature of the present invention, the second retainer component takes the form of an arrest or stop on the frame.

A method for use in laparoscopic surgery comprises, in accordance with the present invention, the steps of (a) providing a retractor instrument comprising an elongate frame and a substantially rigid retractor member movably mounted to the frame, (b) forming an opening in a patient's abdominal wall, (c) inserting the frame and the retractor member through the opening, (d) maintaining the retractor member and the frame in substantially parallel relation to one another during the step of inserting, and (e) upon a partial insertion of the retractor instrument into an abdominal cavity of the patient, manipulating the retractor instrument to shift the retractor member so that the retractor member is angled with respect to the frame. Other steps include (f) manipulating the frame so that the retractor member engages a selected internal body organ of the patient, (g) upon engaging the selected internal body organ with the retractor member, pulling on the frame, and (h) maintaining the retractor member in angled relation with respect to the frame during the step of pulling, whereby the position of the selected internal body organ in the abdominal cavity of the patient is shifted.

In accordance with another feature of the present invention, additional steps of the surgical method include (i) moving the retractor instrument to disengage the retractor member and the selected internal body organ of the patient, (j) upon a disengagement of the retractor member and the internal body organ, manipulating the retractor instrument to shift the retractor member so that the retractor member is again substantially parallel with respect to the frame, and (k) withdrawing the frame and the retractor member from the abdominal cavity of the patient through the opening while maintaining the retractor member and the frame in substantially parallel relation with respect to one another.

Pursuant to another feature of the present invention, step (d) above comprises the step of locking the retractor member to the frame. Preferably, the retractor member is pivotably attached to the frame, whereby upon an unlocking of the retractor member, the retractor member pivots with respect to the frame under the force of gravity. Preferably, the retractor instrument further includes a slider member for locking the retractor member in substantially parallel relation to the frame, the step of unlocking thus including the step of shifting the slider member with respect to the frame.

The present invention provides an improved technique for temporarily displacing an internal body organ of a patient during laparoscopic surgery. A surgical instrument in accordance with the present invention is an effective laparoscopic retractor. It is easy to use and inexpensive to fabricate.

BRIEF DESCRIPTION OF THE DRAWING

FIG. 1 is a schematic longitudinal cross-sectional view of a retractor for use in laparoscopic surgery, in accordance with the present invention, showing a retractor member in a closed or storage configuration.

FIG. 2 is a schematic longitudinal cross-sectional view similar to FIG. 1, showing the retractor member of that drawing figure in an opened or use configuration.

FIG. 3 is a schematic perspective view of another laparoscopic retractor in accordance with the present invention, showing a pair of retractor members in an opened or use configuration.

FIG. 6 is a schematic side perspective view of yet another laparoscopic retractor in accordance with the present invention.

FIG. 8 is partially a perspective view and partially a side elevational view of a further laparoscopic retractor in accordance with the present invention, showing a retractor member in a closed or storage configuration.

FIG. 9 is a view similar to FIG. 8, showing the retractor member of that figure in an opened or use orientation.

FIG. 10 is a perspective view of yet another laparoscopic retractor in accordance with the present invention, showing a retractor member in a closed or storage orientation with respect to a frame member.

FIG. 11 is a view similar to FIG. 10, showing the retractor member of that figure in an opened orientation extending orthogonally with respect to the frame member.

DETAILED DESCRIPTION

Figure 4:
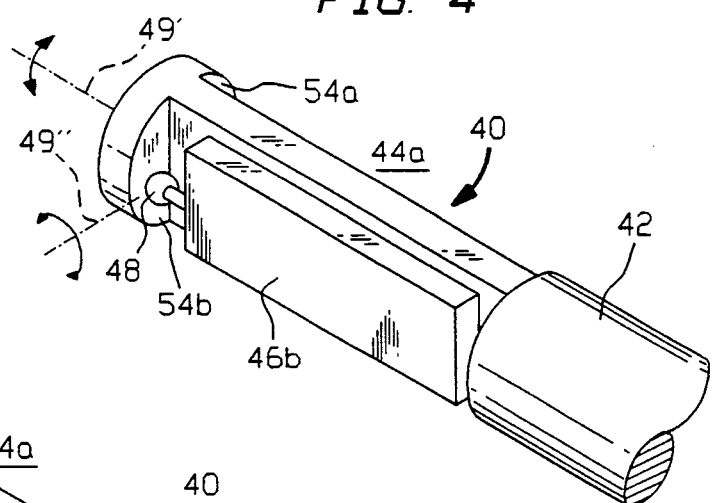
FIG. 4 is a partial perspective view, from a different angle, of the laparoscopic retractor of FIG. 3, showing the retractor members in a closed or storage configuration.

As illustrated in FIGS. 1 and 2, a retractor 20 for use in laparoscopic surgery comprises a substantially rigid frame or body member 22 provided at a distal end with an elongate recess 24 for receiving a substantially rigid retractor arm 26 in a retracted, storage configuration. Retractor arm 26 is swingably mounted to frame or body member 22 at a pivot pin 28. During insertion of the laparoscopic retractor 20 through an opening formed in a patient's abdominal wall (more specifically, through a tubular member traversing the abdominal wall), retractor arm 26 is held in recess 24, in a substantially parallel orientation with respect to frame 22, by a slider element 30. Upon sufficient insertion of the distal end of retractor 20 into the abdominal cavity of the patient, slider 30 is grasped and pulled in a proximal direction via a finger ring 32 or other manual actuator part. The opening of recess 24 due to the sliding away of slider 30 frees retractor arm 26 to swing about pivot pin 28 under the force of gravity, whereby the retractor arm assumes an opened or use configuration shown in FIG. 2.

During a laparoscopic surgical procedure using laparoscopic retractor 20 of FIGS. 1 and 2, an opening is formed in a patient's abdominal wall, for example, through the use of a trocar. A tubular member is inserted through the opening in a conventional technique for maintaining the opening in a dilated state. Upon insertion of frame 22 and retractor arm 26 in the closed, mutually parallel configuration of FIG. 1 through the abdominal opening, slider 30 is shifted in the proximal direction to enable retractor arm 26 to rotate downwardly so that the retractor arm is angled essentially orthogonally with respect to frame 22, as shown in FIG. 2. Frame 22 is then manipulated so that retractor arm 26 engages a selected internal body organ of the patient, such as the liver. Upon engaging the selected internal body organ with retractor arm 26, the operating surgeon or attendant pulls on frame 22 to displace or shift the liver into an at least partially retracted position. During this retraction of the selected internal body organ, retractor arm 26 is maintained in an essentially orthogonal orientation with respect to frame 22 by virtue of an arrest or stop 34 on frame 22, which prevents or blocks further rotation of retractor arm 26.

Upon the completion of a laparoscopic surgical operation on an organ or tissues underlying the retracted organ, frame 22 is moved to disengage retractor arm 26 and the retracted internal body organ of the patient. Upon completing the disengagement of the retractor arm 26 and the internal body organ, the surgeon or attendant rotates retractor instrument 20 so that retractor arm 26 pivots in a reverse direction about pivot pin 28 and again assumes the substantially parallel configuration of FIG. 1. Slider 30 is then shifted in the distal direction to lock retractor arm 26 in recess 24. Frame 22 and retractor arm 26 are then withdrawn from the patient through the abdominal opening.

It is to be noted that it is not necessary for slider 30 to completely close recess 24 in order to lock retractor arm 26 in the closed or parallel configuration of FIG. 1. In fact, slider 30 need only overlap the proximal tip of retractor arm 26. It is to be further noted that retractor arm 26 may be maintained in parallel with respect to frame 22 solely by gravity. In that case, slider 30 may be omitted. During an insertion step of a laparoscopic procedure utilizing such a modified retractor instrument, the frame or body member is held to keep the retractor arm on the upper side. Upon sufficient insertion of the retractor instrument into the patient's abdominal cavity, the frame is rotated to allow the retractor arm to pivot downwardly under the force of gravity.

Figure 5:
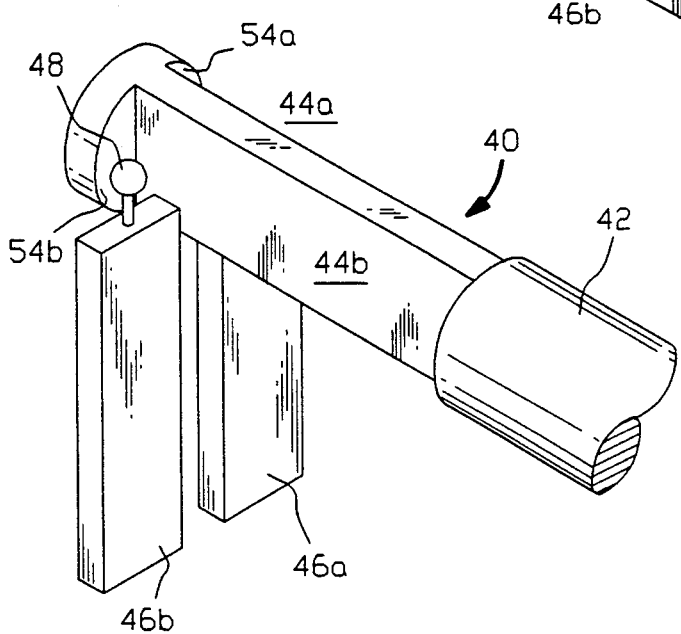
FIG. 5 is a partial perspective view similar to FIG. 4, showing the retractor members in the opened configuration of FIG. 3.

As illustrated in FIGS. 3-5, another retractor instrument 40 comprises an elongate, essentially tubular, frame or body member 42 to a distal end 43 of which a pair of substantially rigid planar retractor arms 46a and 46b are pivotably secured. As shown in FIG. 4, retractor arms 46a and 46b are held in parallel planes in respective recesses or chambers 44a and 44b by respective locking elements 50a and 50b (FIG. 3) which are slidably mounted to frame 42. Retractor arms 46a and 46b are pivotably attached to the distal end 43 of frame 42 via respective universal couplings 48 (only one shown in the drawings). Universal couplings 48 permit retractor arms 46a and 46b to pivot about two axes 49' and 49"

(FIG. 4) upon a proximally directed stroke of locking elements 50a and 50b. Such a stroke of locking elements 50a and 50b opens recesses 44a and 44b and enables retractor arms 46a and 46b to fall under the force of gravity into the essentially orthogonal orientation of FIGS. 3 and 5 wherein arms 46a and 46b are in essentially the same plane. During use of retractor instrument 40 to retract an organ such as the liver, retractor arms 46a and 46b are maintained in their common plane essentially perpendicular to frame 42 by arresting surfaces 54a and 54b at the distal end 43 of frame 42.

It is to be noted that retractor instrument 20 of FIGS. 1 and 2 may be modified to assume specific design features of the embodiment of FIGS. 3-5. For example, retractor arm 26 may be pivotably connected to frame 22 via a universal type coupling. In addition, slider 30 may have an arcuate cross-section like locking elements 50a and 50b, rather than a rectangular cross section.

Similarly, retractor instrument 40 of FIGS. 3-5 may be altered to take on specific design elements shown in the embodiment of FIGS. 1 and 2. For example, retractor instrument 40 might have one integral locking element instead of two separate ones.

Figure 7A:
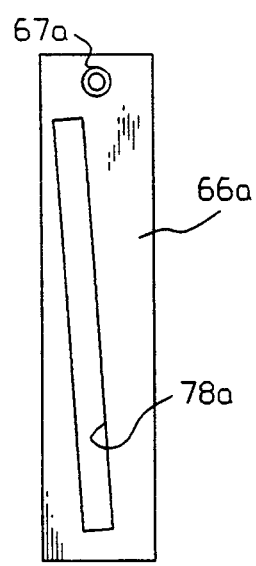
FIGS. 7A-7C are elevational views of three cooperating retractor members shown in FIG. 6.
Figure 7B:
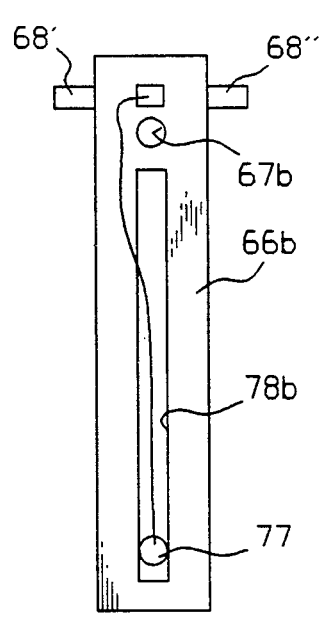
Figure 7C:
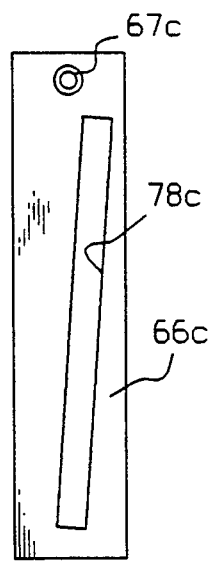

FIGS. 6 and 7A-7C illustrate a further retractor instrument 60. Retractor instrument 60 is provided with three overlapping or interleaved retractor arms 66a, 66b, and 66c. Retractor arms 66a, 66b, and 66c are pivotably mounted to a distal end 63 of a frame or body member 62 via one or two pivot pins 68' and 68" on center retractor arm 66b. Retractor arms 66a, 66b, and 66c are held or locked in a recess or chamber 64 in frame 62 by a cross-sectionally arcuate slider element 70. Outer retractor arms 66a and 66c are pivotably mounted for rotating outwardly in opposite directions in the manner of a fan so that all three retractor arms 66a, 66b, 66c assume a triangular use configuration, as depicted in FIG. 6. Retractor arms 66a and 66c are pivotally connected to retractor arm 66b via mating lugs 67a and 67c which traverse a bore 67b in retractor arm 66b (FIGS. 7A-7C).

It is to be noted that retractor arms or plates 66a and 66c may be pivotally connected to center retractor arm 66b at a point above pivot pins 68' and 68", rather than below the pivot pins, as illustrated in FIGS. 6 and 7A-7C. Alternatively, retractor arms 66a and 66c may be pivotably connected directly to frame 62 via respective universal type couplings (not shown).

To implement the swinging of retractor arms 66a and 66c about an axis 71 extending substantially parallel to frame 62, a wire 75 extends from a finger ring 76 at a proximal end of frame 62 to a pin or peg 77 which traverses camming slots 78a, 78b, and 78c in retractor arms 66a, 66b, and 66c, respectively. Slot 78b extends centrally with respect to center retractor arm 66b, while slots 78a and 78c are inclined with respect to outer retractor arms 66a and 66c. Cable is initially shifted in the distal direction so that peg 77 is located near the free ends of retractor arms 66a, 66b, and 66c while the arms are disposed in a stacked parallel configuration inside recess 64. After slider 70 has been shifted in the proximal direction and after retractor arms 66a, 66b, and 66c have fallen into an orthogonal orientation, wire 75 is pulled in the proximal direction to spread arms 66a, 66b, and 66c. After a laparoscopic surgical operation utilizing retractor instrument 60 is completed, frame 62 is shaken or vibrated to allow peg 75 to fall to the bottoms of slots 78a, 78b, and 78c. Frame 62 is then rotated to swing retractor arms 66a, 66b, and 66c back into the storage position inside recess 64. Slider 70 is then shifted in the distal direction to lock the retractor arms in the closed, storage position and the retractor instrument is withdrawn from the abdominal cavity of the patient.

As shown in FIGS. 8 and 9, an additional retractor instrument 80 comprises a frame or body member 82 defining a recess 84 in which a retractor arm 86 is disposed during a storage or insertion phase of a laparoscopic procedure. A leaf spring 88 is prestressed or biased to maintain retractor arm 86 in recess 84 in a parallel orientation with respect to body member 82, as illustrated in FIG. 8. Leaf spring 88 extends around a lug or rod element 89 and is connected to a cable 90. Upon a pulling of cable 90 via a finger ring 92 attached thereto, leaf spring 88 partially straightens out owing to its being forced along rod element 89, and thereby rotates retractor arm 86 into an essentially orthogonal orientation shown in FIG. 9. The further unbending of leaf spring 88 and the further concomitant rotation of retractor arm 86 is stopped by an arresting surface 94 at the distal end of body member 82. A locking element in the form of a plug 95 bearing at one end two opposing fingers 96a and 96b is connected to cable 90 for locking the cable during a retraction operation. During a withdrawing stoke of cable 90, plug 95 with fingers 96a and 96b passes through an aperture 97 with finger-like extensions 98a and 98b at a proximal end of body member 82. Upon the passage of fingers 96a and 96b outside of body member 82, plug 95 is twisted to angularly displace fingers 96a and 96b with respect to extensions 98a and 98b, thereby locking cable 90 in a fixed position in opposition to the restoring force provided by the spring bias of leaf spring 88. The above-described process is reversed to close retractor instrument 80.

FIGS. 10 and 11 illustrate yet another retractor instrument 100 which comprises a frame or body member 102 defining a recess 104 in which a retractor arm 106 is disposed during a storage or insertion phase of a laparoscopic procedure. A leaf spring 108 is prestressed or biased to maintain retractor arm 106 in recess 104 in a parallel orientation with respect to body member 102, as illustrated in FIG. 10. Leaf spring 108 is fixed to frame member 102 at 109. A push rod 110 provided at a distal end with a wedge 112 is slidably mounted to frame 102. During a retractor opening step, leaf spring 108 is partially straightened out by wedge 112 in response to a distally directed stroke of push rod 110. Retractor ar 106 is thereby rotated into an essentially orthogonal orientation shown in FIG. 11. Further unbending of leaf spring 108 and further concomitant rotation of retractor arm 106 is stopped by an arresting surface 114 at the distal end of body member 102. A locking element in the form of a pin 115 is inserted through openings 116 (only one visible in the drawing) in frame 102 and through an aligned opening in an array of openings 118 in push rod 110, to maintain retractor arm 106 in the opened configuration shown in FIG. 11.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A retractor instrument for use in laparoscopic surgery, comprising:
   an elongate substantially linear frame member having a proximal end and a distal end;
   a substantially rigid retractor member movably mounted to said frame member at a point spaced from said proximal end;
   first retainer means mounted to the frame member for maintaining said retractor member in substantially parallel relation to said frame member during an insertion of the retractor instrument through a patient's abdominal wall and partially into the patient's abdominal cavity in a laparoscopic procedure; and
   second retainer means connected to said frame member for maintaining said retractor member in an angled orientation with respect to said frame member so that said retractor member and said frame member together assume a substantially L shaped configuration during utilization of the retractor instrument to displace an internal body organ of the patient in the laparoscopic procedure.

2. The retractor instrument set forth in claim 1 wherein said frame member is provided at a distal end with a recess for receiving and at least partially enclosing said retractor member during the insertion of the retractor instrument through the patient's abdominal wall and partially into the patient's abdominal cavity.

3. The retractor instrument set forth in claim 2 wherein said first retainer means includes means for locking said retractor member in said recess.

4. The retractor instrument set forth in claim 3 wherein said means for locking includes a slider member slidably mounted to said frame member.

5. The retractor instrument set forth in claim 3 wherein said retractor member is pivotably mounted to said frame member.

6. The retractor instrument set forth in claim 3 wherein said retractor member is pivotably mounted to said frame member via a universal joint.

7. The retractor instrument set forth in claim 3 wherein said second retainer means includes an arrest on said frame member.

8. The retractor instrument set forth in claim 1 wherein said first retainer means includes means for locking said retractor member in a storage configuration parallel to said frame member.

9. The retractor instrument set forth in claim 8 wherein said means for locking includes a slider member slidably mounted to said frame member.

10. The retractor instrument set forth in claim 1 wherein said retractor member is pivotably mounted to said frame member.

11. The retractor instrument set forth in claim 10 wherein said retractor member is pivotably mounted to said frame member via a universal joint.

12. The retractor instrument set forth in claim 1 wherein said second retainer means includes an arrest on said frame member.

13. A retractor instrument for use in laparoscopic surgery, comprising:
   an elongate frame member;
   a plurality of substantially rigid planar retractor members movably mounted to said frame member;
   first retainer means mounted to frame member for maintaining said retractor members in respective spaced parallel planes and in substantially parallel relation to said frame member during an insertion of the retractor instrument through a patient's abdominal wall and partially into the patient's abdominal cavity in a laparoscopic procedure; and
   second retainer means connected to said frame member for maintaining said retractor members substantially in a common plane angled with respect to said frame member during utilization of the retractor instrument to displace an internal body organ of the patient in the laparoscopic procedure.

14. The retractor instrument set forth in claim 13 wherein said retractor members are pivotally connected to said frame member via respective universal type joints spaced from one another, whereby each of said retractor members rotates about two axes during a retractor opening procedure in which said retractor members are each pivoted from a storage configuration maintained by said first retainer means to a use configuration maintained by said second retainer means.

15. A method for use in laparoscopic surgery, comprising the steps of:
   (a) providing a retractor instrument comprising an elongate frame member and a substantially rigid retractor member movably mounted to said frame member;
   (b) forming an opening in a patient's abdominal wall;
   (c) inserting said frame member and said retractor member through said opening;
   (d) maintaining said retractor member and said frame member in substantially parallel relation to one another during said step of inserting;
   (e) upon a partial insertion of the retractor instrument into an abdominal cavity of the patient, manipulating the retractor instrument to shift said retractor member so that said retractor member is angled with respect to said frame member;
   (f) manipulating said frame member so that said retractor member engages a selected internal body organ of the patient;
   (g) upon engaging the selected internal body organ with said retractor member, exerting a force on said frame member; and
   (h) maintaining said retractor member in an angled orientation with respect to said frame member during said step of exerting, whereby the position of the selected internal body organ in the abdominal cavity of the patient is shifted.

16. The method set forth in claim 15 wherein said step (d) comprises the step of locking said retractor member to said frame member.

17. The method set forth in claim 16 wherein said retractor member is pivotably attached to said frame member, said step (e) comprising the step of unlocking said retractor member, whereby said retractor member pivots under the force of gravity.

18. The method set forth in claim 17 wherein said retractor instrument further includes a slider member for locking said retractor member in substantially parallel relation to said frame member, said step of unlocking including the step of shifting said slider member with respect to said frame member.

19. The method set forth in claim 15, further comprising the steps of:
   (i) moving the retractor instrument to disengage said retractor member and the selected internal body organ of the patient;
   (j) upon a disengagement of the retractor member and the internal body organ, manipulating the retractor instrument to shift said retractor member so that said retractor member is again substantially parallel with respect to said frame member; and (k) withdrawing said frame member and said retractor member from the abdominal cavity of the patient through said opening while maintaining said retractor member and said frame member in substantially parallel relation with respect to one another.

20. The method set forth in claim 19 wherein said retractor member is pivotably attached to said frame member, said step (j) including the step of rotating said frame member about a longitudinal axis, whereby said retractor member pivots under the force of gravity from an extended angled orientation to a closed orientation substantially parallel to said frame member.

21. A retractor instrument for use in laparoscopic surgery, comprising:

an elongate frame member;

a retractor member movably mounted to said frame member;

first retainer means mounted to frame member for maintaining said retractor member in substantially parallel relation to said frame member during an insertion of the retractor instrument through a patient's abdominal wall and partially into the patient's abdominal cavity in a laparoscopic procedure, said first retainer means including means for locking said retractor member in a storage configuration parallel to said frame member; and second retainer means connected to said frame member for maintaining at least a portion of said retractor member in an angled orientation with respect to said frame member during utilization of the retractor instrument to displace an internal body organ of the patient in the laparoscopic procedure.

22. The retractor instrument set forth in claim 21 wherein said means for locking includes a slider member slidably mounted to said frame member.

23. A retractor instrument for use in laparoscopic surgery, comprising:

an elongate frame member having a proximal end and a distal end;

a substantially rigid retractor member movably mounted to said frame member at a point spaced from said proximal end, said retractor member having a substantially planar surface;

first retainer means mounted to frame member for maintaining said retractor member in substantially parallel relation to said frame member during an insertion of the retractor instrument through a patient's abdominal wall and partially into the patient's abdominal cavity in a laparoscopic procedure; and second retainer means connected to said frame member for maintaining said retractor member in an angled orientation with respect to said frame member so that said planar surface of said retractor member is engageable with an internal body organ of the patient to enabling a shifting of the organ.

24. A retractor instrument for use in laparoscopic surgery, comprising:

an elongate frame member having a proximal end and a distal end;

a substantially rigid retractor member pivotably mounted to said frame member at a single point spaced from said proximal end;

first retainer means mounted to frame member for maintaining said retractor member in substantially parallel relation to said frame member during an insertion of the retractor instrument through a patient's abdominal wall and partially into the patient's abdominal cavity in a laparoscopic procedure, said retractor member being free to swing about said pivot point under the action of gravity upon a de-actuation of said first retainer means; and second retainer means connected to said frame member for maintaining said retractor member in an angled orientation with respect to said frame member during utilization of the retractor instrument to displace an internal body organ of the patient in the laparoscopic procedure.

* * * * *